(12) United States Patent
Wollenberg et al.

(10) Patent No.: US 7,405,185 B2
(45) Date of Patent: Jul. 29, 2008

(54) PROCESS FOR MAKING GROUP II METAL OVERBASED SULFURIZED ALKYLPHENOLS

(75) Inventors: Robert H. Wollenberg, Orinda, CA (US); Steven G. Lockett, San Rafael, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 559 days.

(21) Appl. No.: 10/672,721

(22) Filed: Sep. 26, 2003

(65) Prior Publication Data
US 2005/0070451 A1 Mar. 31, 2005

(51) Int. Cl.
*C10M 159/22* (2006.01)
*C10M 159/24* (2006.01)

(52) U.S. Cl. ...................... 508/574; 508/391
(58) Field of Classification Search .......... 508/574, 508/391
See application file for complete search history.

(56) References Cited

U.S. PATENT DOCUMENTS

| | | | |
|---|---|---|---|
| 3,178,368 A | 4/1965 | Hanneman | |
| 3,367,867 A | 2/1968 | Abbott et al. | |
| 3,801,507 A | 4/1974 | Hendrickson et al. | |
| 4,251,379 A | 2/1981 | Le Coent et al. | |
| 4,302,342 A | 11/1981 | Demoures et al. | |
| 4,465,603 A | 8/1984 | Koch et al. | |
| 4,744,921 A | 5/1988 | Liston | |
| 4,865,754 A * | 9/1989 | Chang ................. | 508/392 |
| 4,927,551 A * | 5/1990 | Erdman et al. ............. | 508/291 |
| 5,318,710 A | 6/1994 | Campbell | |
| 5,320,762 A | 6/1994 | Campbell | |
| 5,529,705 A | 6/1996 | Small, Jr. et al. | |
| 5,677,270 A | 10/1997 | Small, Jr. et al. | |
| 5,714,443 A | 2/1998 | Cane et al. | |
| 5,716,914 A | 2/1998 | Cane et al. | |
| 6,187,972 B1 * | 2/2001 | Kawabe et al. ............. | 568/858 |

FOREIGN PATENT DOCUMENTS

| | | |
|---|---|---|
| EP | 0 259 974 B2 | 3/1997 |
| EP | 0 989 178 A1 | 3/2000 |
| GB | 2197336 A * | 5/1988 |

* cited by examiner

*Primary Examiner*—Patrick Niland
(74) *Attorney, Agent, or Firm*—Sarita R. Kelley (57) ABSTRACT

The present invention is directed to a novel process for making Group II metal overbased sulfurized alkylphenols, which process uses alkylene carbonate as both a source of carbon dioxide and alkylene glycol. In particular, under the reaction conditions using ethylene carbonate, carbonation time is reduced to about one quarter the time taught in the prior art to make Group II metal overbased sulfurized alkylphenol compositions. The present invention is also directed to a detergent-dispersant additive composition comprising a Group II metal overbased sulfurized alkylphenols, wherein the Group II metal overbased sulfurized alkylphenols have a reduced color as measured by ASTM Test No. D 6045 and an increased hydrolytic stability as measured by a modified ASTM Test No. 2619. The present invention is also directed to a process using ethylene carbonate or alkyl-substituted ethylene carbonate and water for delivering in situ equimolar quantities of ethylene glycol and carbon dioxide for use as reactants in chemical reactions.

62 Claims, 2 Drawing Sheets

PROCESS FOR MAKING GROUP II METAL OVERBASED SULFURIZED ALKYLPHENOLS

FIELD OF THE INVENTION

This invention is directed to a novel process for making Group II metal overbased sulfurized alkylphenols, which process uses ethylene carbonate as both a source of carbon dioxide and ethylene glycol. In particular, under the reaction conditions using ethylene carbonate, carbonation time is reduced to one quarter or less than time taught in the prior art to make Group II metal overbased sulfurized alkylphenol compositions. The present invention is also directed to a detergent-dispersant additive composition comprising Group II metal overbased sulfurized alkylphenols, wherein the Group II metal overbased sulfurized alkylphenols have a color of 3.5 or lower, as measured using ASTM Test No. D 6045, and increased hydrolytic stability as measured by a modified ASTM Test No. 2619, wherein the TBN of the Group II metal overbased sulfurized alkylphenols decreases less than 10 percent, and preferably less than 8 percent, after the addition of 2.0 percent water and after 6 days at 80° C. The present invention is also directed to a process using ethylene carbonate or alkyl-substituted ethylene carbonate and water for delivering in situ equimolar quantities of ethylene glycol and carbon dioxide for use as reactants in chemical reactions.

BACKGROUND OF THE INVENTION

The operation of diesel and spark ignition internal combustion engines is typically accompanied by the formation of sludge, lacquer and resinous deposits which adhere to the moving engine parts and thereby reduce engine efficiency. In order to prevent or reduce the formation of these deposits, a wide variety of chemical additives have been developed for incorporation into lubricating oils. These additives are commonly referred to as detergents and dispersants. Dispersants have the ability to keep deposit forming materials suspended in the oil so as to retard deposit formation during engine operation. Detergents have the ability to remove preexisting deposits from the engine during engine operation and to neutralize acids in railroad, marine and automotive engines.

Among the many additives which have been developed for this purpose, Group II metal overbased sulfurized alkylphenol compositions have been found to be highly effective detergent/dispersants for use in lubricating oils. Furthermore, these additives are excellent oxidation and corrosion inhibitors and, by virtue of their alkalinity reserve, have the ability to neutralize acidic combustion and oxidation products. Such acidic products form during engine operation, particularly when operated on high sulfur containing fuels, and tend to accumulate in the lubricating oil. The sulfur in these compositions has antioxidant activity.

The ability of Group II metal overbased sulfurized alkylphenol compositions to neutralize such acidic products can be directly measured by determining the total base number (TBN) of the composition. Higher TBNs reflect a greater capacity for these compositions to neutralize acids generated during engine operation. The term "overbased" is used to describe those sulfurized alkaline earth metal alkylphenates in which the ratio of the number of equivalents of the alkaline earth metal moiety to the number of equivalents of the phenol moiety is greater than one, and is usually greater than 1.2 and may be as high as 4.5 or greater. In contrast, the equivalent ratio of alkaline earth metal moiety to phenol moiety in "neutral" alkaline earth metal sulfurized alkylphenol is 1. Thus, the "overbased" material typically contains greater than 20% in excess of the alkaline earth metal present in the corresponding "neutral" material. For this reason, "overbased" alkaline earth metal sulfurized alkylphenol has a greater capability for neutralizing acidic matter than does the corresponding "neutral" alkaline earth metal sulfurized alkylphenol.

The preparation of Group II metal overbased sulfurized alkylphenate compositions is well known in the art. A number of patents have discussed processes in which overbasing is accomplished by the direct addition of ethylene glycol and carbon dioxide.

For example, U.S. Pat. No. 3,178,368 discloses the basic process for making metal overbased alkylphenates using an alkylphenol, a sulfonate, a high molecular weight alcohol, lubricating oil, sulfur, hydrated lime (or calcium oxide), ethylene glycol and carbon dioxide. The metal overbased sulfurized alkylphenates prepared by this process have greater than 20% metal compared to the neutral alkylphenates.

U.S. Pat. No. 3,367,867 discloses the preparation of low-foaming metal overbased alkylphenates by starting with alkylphenols wherein the alkyl group is a mixture of straight and branched chain alkyl groups.

U.S. Pat. No. 3,801,507 discloses sulfurized metal alkylphenates that have a ratio of sulfur to calcium between 1 and 2 which provides for better dispersancy and improved antioxidant activity.

U.S. Pat. No. 4,251,379 discloses a process for increasing the TBN of metal overbased sulfurized alkylphenates to more than 250.

U.S. Pat. No. 4,744,921 discloses the use of a sulfurization catalyst in the preparation of metal overbased sulfurized alkylphenates to obtain products having a lower crude sediment and TBN greater than 300.

U.S. Pat. No. 5,320,762 discloses the use of alkylphenols having a substantially straight chain alkyl substituent attached to the phenol ring in a middle position to obtain metal overbased sulfurized alkylphenates which possess low viscosity at high TBNs.

U.S. Pat. Nos. 5,714,443 and 5,716,914 disclose the preparation and use of metal overbased sulfurized alkylphenates modified by incorporation of a mono-carboxylic acid or a di- or polycarboxylic acid in lubricating oils. Also disclosed is the use of a metal halide catalyst to increase the TBN in the metal overbased sulfurized alkylphenate product.

European Patent No. 259974 discloses a process for the preparation of Group II overbased sulfurized alkylphenols characterized as possessing a TBN of 300 or greater and having viscosities less than 1000 cSt at 100° C. In particular, This patent teaches that the hydrolytic stability of the overbased sulfurized alkylphenols is improved by the use of a sulfurization catalyst, such as 2-mercaptobenzothiozole and derivatives thereof.

European Patent No. 989178 discloses a process for the preparation of an overbased alkaline earth metal phenate sulfide having a high base number and good hydrolytic stability.

U.S. Pat. No. 4,465,603 discloses the replacement of the ethylene glycol employed in the overbasing step in the preparation of metal overbased sulfurized alkylphenates with dimethyl carbonate. It is believed that the hydrolysis products of dimethyl carbonate are likely carbon dioxide and methyl alcohol.

Typically, Group II metal overbased sulfurized alkylphenol compositions are prepared by treating alkylphenol in a suitable diluent (e.g., a lubricating oil) with an amount of an alkaline earth metal hydroxide, oxide and/or alkoxide in excess of that necessary to neutralize the phenol and then sulfurizing the resulting product, optionally in the presence of a sulfurizing catalyst. The sulfurized product is then treated with carbon dioxide to provide the Group II metal overbased sulfurized alkylphenol composition.

Such Group II metal overbased sulfurized alkylphenols are useful for preparing additive compositions which are further used to prepare a fully formulated lubricant composition suitable for use in an internal combustion engine. Typically, the additive composition is prepared as a concentrate and is then shipped to a point where it is used to prepare fully formulated lubricant compositions by combining requisite amounts of several additive compositions, including a Group II metal overbased sulfurized alkylphenol composition, to a base stock.

In order to reduce shipping costs, the Group II metal overbased sulfurized alkylphenol is preferably prepared to contain as little diluent as possible. Additionally, in order to achieve the maximum amount of acid neutralization possible, the Group II metal overbased sulfurized alkylphenol is preferably prepared to contain as high a TBN as possible.

Thus, while Group II metal overbased sulfurized alkylphenols produced in the prior art are reported to possess TBNs of up to about 350 or more, in practice, commercial Group II metal overbased sulfurized alkylphenols typically have a TBN of less than about 300, and more typically less than about 275, so as to ensure that the composition possesses acceptable viscosity because viscosity typically increases with an increase in the TBN. In view of the above, it is generally desirable to increase the TBN of the Group II metal overbased sulfurized alkylphenols.

The chemistry in the conventional preparation of overbased sulfurized alkylphenols begins with the reaction of lime (calcium hydroxide) and the alkylphenol to form calcium phenate with the aid of ethylene glycol as a promoter. This reaction typically begins at approximately 135° C., with the generation of water. The calcium phenate quickly reacts with sulfur in a reaction that cross-links the alkylphenol aromatic rings. At this point, the reaction is ready for carbonation.

The conventional carbonation process uses carbon dioxide and ethylene glycol for the preparation of overbased sulfurized alkylphenols. The key change in the present process is the replacement of the carbon dioxide/ethylene glycol carbonation process with a simpler and faster ethylene carbonate process. Ethylene carbonate serves as a source of equal molar quantities of carbon dioxide and ethylene glycol through hydrolysis.

Optimization of processing properties for highly overbased sulfurized alkylphenols is highly empirical, owing to the high degree of overbasing which causes the overbased sulfurized phenol compositions to be less stable and, accordingly, more susceptible to degradation. Carbonation of sulfurized alkylphenols by the prior art process is the most time consuming processing step for production of overbased sulfurized alkylphenols. This is because gaseous carbon dioxide must be added carefully and slowly at the right temperature. For example, if carbon dioxide is charged too rapidly, a portion of the gas can simply escape through the reactor to the atmosphere or vent. In such a case, insufficient carbon dioxide will ultimately be delivered to the reactor resulting in high crude sediment. Fundamentally, this is an issue of mixing and reaction rate, because the gaseous carbon dioxide must be added to the reactor at temperatures far above the boiling point. A further complication may arise if the carbon dioxide is inadequately dispersed in the reaction mixture. This can occur if the reactor does not have sufficient agitation relative to the rate of gas introduction. Inadequate agitation can result in "local over-carbonation" which can result in poor product performance such as hydrolytic stability.

Overbased sulfurized alkylphenol carbonation is a complex process and is highly dependent on reaction conditions. The reactions involved are subtle and not perfectly understood. For example, glycol plays a critical role in this process and the overbased sulfurized alkylphenol undergoes oxidation with subsequent condensation of the reaction intermediates.

The use of ethylene carbonate in the carbonation process of the present invention is advantageous because it eliminates the problems of timing the addition of carbon dioxide, adequately dispersing it, and correctly charging the ethylene glycol. This is because the hydrolysis of ethylene carbonate to ethylene glycol and carbon dioxide occurs in situ which results in the carbon dioxide produced to be completely dispersed in the reaction medium.

It is believed that the present rapid carbonation process for overbasing sulfurized alkylphenols using ethylene carbonate instead of ethylene glycol and carbon dioxide can also be used for the preparation of highly overbased alkyl aromatic salicylic acid, sulfurized alkyl aromatic salicylic acid, and alkyl aromatic sulfonic acid and mixtures thereof with advantages similar to those observed for the preparation of overbased sulfurized alkyl phenol compositions.

SUMMARY OF THE INVENTION

The present invention is directed toward a process for preparing Group II metal overbased sulfurized alkylphenols. The present invention is also directed to a detergent-dispersant additive composition comprising Group II metal overbased sulfurized alkylphenols, wherein the Group II metal overbased sulfurized alkylphenols have a color of 3.5 or lower, as measured by ASTM Test No. D 6045. The Group II metal overbased sulfurized alkylphenols also have increased hydrolytic stability as measured by a modified ASTM Test No. 2619, wherein the TBN of the Group II metal overbased sulfurized alkylphenols decreases less than 10 percent, and preferably less than 8 percent, after the addition of 2.0 percent water and after 6 days at 80° C. The present invention is also directed to a process using ethylene carbonate or alkyl-substituted ethylene carbonate and water for delivering in situ equimolar quantities of ethylene glycol and carbon dioxide for use as reactants in chemical reactions.

In particular, the process of the present invention for preparing Group II metal overbased sulfurized alkylphenols comprises:

forming a reaction mixture by combining a sulfurized alkylphenol wherein the alkyl group contains a sufficient number of carbon atoms to render oil-soluble the resulting Group II metal overbased sulfurized alkylphenol, an alkanol containing about 6 to about 15 carbon atoms, a Group II metal oxide, hydroxide or $C_1$-$C_6$ alkoxide, a $C_2$-$C_{10}$ alkylene glycol and with an alkylene carbonate selected from ethylene carbonate or a mono-alkyl or di-alkyl substituted ethylene carbonate, said alkylene carbonate having the following structure:

wherein $R_1$ and $R_2$ are independently hydrogen or alkyl containing one to three carbon atoms; and wherein the contacting is carried out for a time and at a temperature sufficient to form in situ carbon dioxide and alkylene glycol, or a reacting equivalent, to form a product comprising a Group II earth metal overbased sulfurized alkylphenol.

In the alkylene carbonate structure above, preferably one of $R_1$ and $R_2$ is hydrogen and the other is hydrogen or methyl. In other words, the alkylene carbonate is preferably ethylene carbonate or propylene carbonate. More preferably, $R_1$ and $R_2$ are both hydrogen; that is, the alkylene carbonate is ethylene carbonate.

The sulfurized alkylphenol in the reaction mixture of the present process may be replaced with a Group II metal sulfurized alkylphenate.

The reaction mixture of the present process further comprises an oil-soluble Group II metal overbased natural or synthetic hydrocarbyl sulfonic acid, sulfonate, or mixtures thereof.

The alkylene carbonate is added to the reaction mixture over a time period of about 5 minutes to about 120 minutes, preferably the alkylene carbonate is added to the reaction mixture over a time period of about 15 minutes to about 90 minutes, and more preferably the alkylene carbonate is added to the reaction mixture over a time period of about 30 minutes to about 60 minutes.

The process of the present invention is typically conducted at about 150° C. to about 215° C., preferably conducted at from about 160° C. to about 200° C., and more preferably conducted at from about 170° C. to about 190° C.

The alkyl group of the mono-alkyl or di-alkyl substituted ethylene carbonate useful for carrying out the process of the present invention is preferably a mono-substituted methyl group, i.e., the alkylene carbonate is propylene carbonate. Most preferably, the alkylene carbonate is ethylene carbonate.

The alkyl group of the alkylphenol and the alkyl phenate employed in the process of the instant invention contains a sufficient number of carbon atoms to render the Group II metal overbased sulfurized alkylphenol oil-soluble. In general, alkyl groups of about 8 carbon atoms or more are sufficient to render the Group II metal overbased sulfurized alkylphenol oil-soluble.

Furthermore, in a preferred embodiment, the alkyl group of the alkylphenol and the alkyl phenate is attached predominantly at the para position of the phenol ring. Preferably, the alkylphenol and the alkyl phenate containing the para attachment of the alkyl group is from about 75 to about 95 weight percent of the total alkylphenol and the alkyl phenate. More preferably, the alkylphenol and the alkyl phenate containing the para attachment of the alkyl group is from about 80 to about 95 weight percent of the total alkylphenol and the alkyl phenate.

In one preferred embodiment, the alkyl group of said alkylphenol and the alkyl phenate contains from 25 to 100 mole percent predominantly straight-chain alkyl groups of from 15 to 35 carbon atoms and from 75 to 0 mole percent of the alkyl groups are branched-chain, such as polypropenyl, of from 9 to 18 carbon atoms. More preferably, the alkyl group of said alkylphenol and the alkyl phenate contains from 35 to 100 mole percent predominantly straight-chain alkyl groups of from 15 to 35 carbon atoms and from 65 to 0 mole percent of the alkyl groups are branched-chain, such as polypropenyl, of from 9 to 18 carbon atoms. In yet another preferred embodiment, the alkyl group of said alkylphenol and the alkyl phenate contains from 40 to 70 mole percent predominantly straight-chain alkyl groups of from 15 to 35 carbon atoms and from 60 to 30 mole percent of the alkyl groups are branched-chain, such as polypropenyl, of from 9 to 18 carbon atoms. Most preferably, the alkyl group of said alkylphenol and the alkyl phenate contains approximately 50 mole percent predominantly straight-chain alkyl groups of from 15 to 35 carbon atoms and approximately 50 mole percent of the alkyl groups are branched-chain, such as polypropenyl, of from 9 to 18 carbon atoms.

The preferred oil-soluble Group II metal overbased natural or synthetic hydrocarbyl sulfonic acid, sulfonate, or mixture thereof useful for the process of the present invention are single-ring alkyl aromatic hydrocarbyl sulfonic acid, sulfonate, or mixture thereof, more preferred are alkylbenzene or alkyltoluene sulfonic acids, sulfonates or mixtures thereof. The alkyl group on the aromatic ring can be from about 6 to about 60 carbon atoms. Preferably, the alkyl group is from about 10 to about 40 carbon atoms and most preferably from about 20 to about 28 carbon atoms.

In the process of the present invention, the Group II metal oxide, hydroxide or $C_1$-$C_6$ alkoxide is selected from the group consisting of calcium, barium, magnesium and strontium oxide, hydroxide or $C_1$-$C_6$ alkoxide and mixtures thereof. Preferably, the Group II metal oxide, hydroxide or $C_1$-$C_6$ alkoxide is Dolomite comprising $Ca(OH)_2 \cdot Mg(OH)_2$. Most preferably, the Group II metal oxide, hydroxide or $C_1$-$C_6$ alkoxide is calcium hydroxide.

As used herein, the term "Group II metal" means calcium, barium, magnesium, and strontium. Preferably, the Group II metal is selected from the group consisting of calcium, magnesium, barium, and mixtures thereof. Most preferably, the Group II metal is calcium.

In the present process, the alkanol contains at least 6 carbon atoms, and typically from about 8 to about 13 carbon atoms. Preferably, the alkanol is isodecyl alcohol.

An optional step of the process of the present invention comprises heating the reaction mixture under reduced pressure to remove a portion of the unreacted $C_2$-$C_{10}$ alkylene glycol and carbon dioxide. This step is preferably conducted at a temperature sufficient to effect removal of a portion of the water in the reaction system without additionally removing significant amounts, i.e., greater than about 15%, of either the alkanol containing 6 to 18 carbon atoms and the $C_2$-$C_{10}$ alkylene glycol. This step is typically conducted at from about 175° C. to about 220° C., and preferably conducted at from about 200° C. to about 215° C.

The $C_2$-$C_{10}$ alkylene glycol of the present process is preferably ethylene glycol.

An alternate embodiment of the present process for preparing Group II metal overbased sulfurized alkylphenols comprises the steps of:

(a) forming a reaction mixture by combining a sulfurized alkylphenol wherein the alkyl group contains a sufficient number of carbon atoms to render oil-soluble the resulting Group II metal overbased sulfurized alkylphenol, an alkanol containing about 6 to about 15 carbon atoms, a Group II metal oxide, hydroxide or $C_1$-$C_6$ alkoxide, and a $C_2$-$C_{10}$ alkylene glycol; and (b) contacting said reaction mixture with an alkylene carbonate selected from ethylene carbonate or a mono-alkyl or di-alkyl substituted ethylene carbonate, said alkylene carbonate having the following structure:

wherein $R_1$ and $R_2$ are independently hydrogen or alkyl containing one to three carbon atoms; and wherein the contacting is carried out for a time and at a temperature sufficient to form in situ carbon dioxide and alkylene glycol, or a reacting equivalent, to form a product comprising a Group II earth metal overbased sulfurized alkylphenol.

In the alkylene carbonate structure above, preferably one of $R_1$ and $R_2$ is hydrogen and the other is hydrogen or methyl. In other words, the alkylene carbonate is preferably ethylene carbonate or propylene carbonate. More preferably, $R_1$ and $R_2$ are both hydrogen; that is, the alkylene carbonate is ethylene carbonate.

The sulfurized alkylphenol in the reaction mixture of the present process may be replaced with a Group II metal sulfurized alkylphenate.

The reaction mixture of the present process further comprises an oil-soluble Group II metal overbased natural or synthetic hydrocarbyl sulfonic acid, sulfonate, or mixtures thereof.

The alkylene carbonate is added to the reaction mixture over a time period of about 5 minutes to about 120 minutes, preferably the alkylene carbonate is added to the reaction mixture over a time period of about 15 minutes to about 90 minutes, and more preferably the alkylene carbonate is added to the reaction mixture over a time period of about 30 minutes to about 60 minutes.

Step (b) is typically conducted at about 150° C. to about 215° C., preferably conducted at from about 160° C. to about 200° C., and more preferably conducted at from about 170° C. to about 190° C.

The alkyl group of the mono-alkyl or di-alkyl substituted ethylene carbonate useful for carrying out the process of the present invention is preferably a mono-substituted methyl group, i.e., the alkylene carbonate is propylene carbonate. Most preferably, the alkylene carbonate is ethylene carbonate.

The alkyl group of the alkylphenol and the alkyl phenate employed in the process of the instant invention contains a sufficient number of carbon atoms to render the Group II metal overbased sulfurized alkylphenol oil-soluble. In general, alkyl groups of about 8 carbon atoms or more are sufficient to render the Group II metal overbased sulfurized alkylphenol oil-soluble.

Furthermore, in a preferred embodiment, the alkyl group of the alkylphenol and the alkyl phenate is attached predominantly at the para position of the phenol ring. Preferably, the alkylphenol and the alkyl phenate containing the para attachment of the alkyl group is from about 75 to about 95 weight percent of the total alkylphenol and the alkyl phenate. More preferably, the alkylphenol and the alkyl phenate containing the para attachment of the alkyl group is from about 80 to about 95 weight percent of the total alkylphenol and the alkyl phenate.

In one preferred embodiment, the alkyl group of said alkylphenol and the alkyl phenate contains from 25 to 100 mole percent predominantly straight-chain alkyl groups of from 15 to 35 carbon atoms and from 75 to 0 mole percent of the alkyl groups are branched-chain, such as polypropenyl, of from 9 to 18 carbon atoms. More preferably, the alkyl group of said alkylphenol and the alkyl phenate contains from 35 to 100 mole percent predominantly straight-chain alkyl groups of from 15 to 35 carbon atoms and from 65 to 0 mole percent of the alkyl groups are branched-chain, such as polypropenyl, of from 9 to 18 carbon atoms. In yet another preferred embodiment, the alkyl group of said alkylphenol and the alkyl phenate contains from 40 to 70 mole percent predominantly straight-chain alkyl groups of from 15 to 35 carbon atoms and from 60 to 30 mole percent of the alkyl groups are branched-chain, such as polypropenyl, of from 9 to 18 carbon atoms. Most preferably, the alkyl group of said alkylphenol and the alkyl phenate contains approximately 50 mole percent predominantly straight-chain alkyl groups of from 15 to 35 carbon atoms and approximately 50 mole percent of the alkyl groups are branched-chain, such as polypropenyl, of from 9 to 18 carbon atoms.

The preferred oil-soluble Group II metal overbased natural or synthetic hydrocarbyl sulfonic acid, sulfonate, or mixture thereof useful for the process of the present invention are single-ring alkyl aromatic hydrocarbyl sulfonic acid, sulfonate, or mixture thereof, more preferred are alkylbenzene or alkyltoluene sulfonic acids, sulfonates or mixtures thereof. The alkyl group on the aromatic ring can be from about 6 to about 60 carbon atoms. Preferably, the alkyl group is from about 10 to about 40 carbon atoms and most preferably from about 20 to about 28 carbon atoms.

In the process of the present invention, the Group II metal oxide, hydroxide or $C_1$-$C_6$ alkoxide is selected from the group consisting of calcium, barium, magnesium and strontium oxide, hydroxide or $C_1$-$C_6$ alkoxide and mixtures thereof. Preferably, the Group II metal oxide, hydroxide or $C_1$-$C_6$ alkoxide is Dolomite comprising $Ca(OH)_2.Mg(OH)_2$. Most preferably, the Group II metal oxide, hydroxide or $C_1$-$C_6$ alkoxide is calcium hydroxide.

As used herein, the term "Group II metal" means calcium, barium, magnesium, and strontium. Preferably, the Group II metal is selected from the group consisting of calcium, magnesium, barium, and mixtures thereof. Most preferably, the Group II metal is calcium.

In the present process, the alkanol contains at least 6 carbon atoms, and typically from about 8 to about 13 carbon atoms. Preferably, the alkanol is isodecyl alcohol.

An optional step of the process of the present invention comprises heating the reaction mixture under reduced pressure to remove a portion of the unreacted $C_2$-$C_{10}$ alkylene glycol and carbon dioxide. This step is preferably conducted at a temperature sufficient to effect removal of a portion of the water in the reaction system without additionally removing significant amounts, i.e., greater than about 15%, of either the alkanol containing 6 to 18 carbon atoms and the $C_2$-$C_{10}$ alkylene glycol. This step is typically conducted at from about 175° C. to about 220° C., and preferably conducted at from about 200° C. to about 215° C.

The $C_2$-$C_{10}$ alkylene glycol of the present process is preferably ethylene glycol.

Another alternate embodiment of the process of the present invention comprises the steps of:
(a) forming a first reaction mixture by combining an alkylphenol wherein the alkyl group contains a sufficient number of carbon atoms to render oil-soluble the resulting Group II metal overbased sulfurized alkylphenol, an oil-soluble Group II metal overbased natural or synthetic hydrocarbyl sulfonic acid, sulfonate, or mixtures thereof, and an alkanol containing about 6 to about 18 carbon atoms, the temperature of said first reaction mixture being at least about 40° C.;
(b) contacting said first reaction mixture with a second reaction mixture comprising a Group II metal oxide, hydroxide or $C_1$-$C_6$ alkoxide; a sulfurization agent and an inert hydrocarbon diluent at a temperature and for a time sufficient to effect sulfurization of the alkylphenol to form a third reaction mixture;
(c) contacting said third reaction mixture with a $C_2$-$C_{10}$ alkylene glycol to form a fourth reaction mixture; and (d) contacting said fourth reaction mixture with an alkylene carbonate selected from ethylene carbonate or a mono-alkyl or di-alkyl substituted ethylene carbonate, wherein the alkylene carbonate has the following formula:

wherein $R_1$ and $R_2$ are independently hydrogen or alkyl containing one to three carbon atoms; and wherein said contacting is carried out for a time and at a temperature sufficient to form in situ carbon dioxide and alkylene glycol, or a reacting equivalent, to form a product comprising a Group II earth metal overbased sulfurized alkylphenol.

In step (c), after contacting the third reaction mixture with a $C_2$-$C_{10}$ alkylene glycol, the temperature of the system is preferably raised, if necessary, from that of step (b) to between about 120° C. and about 190° C. Also in step (c), the $C_2$-$C_{10}$ alkylene glycol addition is preferably conducted at from about 100° C. to about 190° C., and even more preferably at from 125° C. to 165° C.

In step (d), the temperature is maintained below about 215° C. and the ethylene carbonate is added to the fourth reaction mixture over a time period of about 5 minutes to about 120 minutes, preferably over a time period of about 15 minutes to about 90 minutes, and more preferably over a time period of about 30 minutes to about 60 minutes.

Step (d) is typically conducted at about 150° C. to about 215° C., preferably conducted at from about 160° C. to about 200° C., and more preferably conducted at from about 170° C. to about 190° C.

In the alkylene carbonate structure above, preferably one of $R_1$ and $R_2$ is hydrogen and the other is hydrogen or methyl. In other words, the alkylene carbonate is preferably ethylene carbonate or propylene carbonate. More preferably, $R_1$ and $R_2$ are both hydrogen; that is, the alkylene carbonate is ethylene carbonate.

An optional step (e) comprises heating the fourth reaction mixture of step (d) under reduced pressure to remove a portion of the unreacted $C_2$-$C_{10}$ alkylene glycol and carbon dioxide. Step (e) is preferably conducted at a temperature sufficient to effect removal of a portion of the water in the reaction system without additionally removing significant amounts, i.e., greater than about 15%, of either the alkanol containing 6 to 18 carbon atoms and the $C_2$-$C_{10}$ alkylene glycol. Step (e) is typically conducted at from about 175° C. to about 220° C., and preferably conducted at from about 200° C. to about 215° C.

This embodiment of the process of the present invention further optionally comprises in step (a) or in step (b), or in both steps (a) and (b), a sulfurization catalyst, wherein the sulfurization catalyst is preferably a hydrogen halide, an ammonium halide, a metal halide or 2-mercaptobenzothiozole. More preferably, the catalyst is a metal halide, and even more preferably calcium chloride.

The alkyl group of the alkylphenol employed in the process of the instant invention contains a sufficient number of carbon atoms to render the Group II metal overbased sulfurized alkylphenol oil-soluble. In general, alkyl groups of about 8 carbon atoms or more are sufficient to render the Group II metal overbased sulfurized alkylphenol oil-soluble.

Furthermore, in a preferred embodiment, the alkyl group of the alkylphenol is attached predominantly at the para position of the phenol ring. Preferably, the alkylphenol containing the para attachment of the alkyl group is from about 75 to about 95 weight percent of the total alkylphenol. More preferably, the alkylphenol containing the para attachment of the alkyl group is from about 80 to about 95 weight percent of the total alkylphenol.

In one preferred embodiment, the alkyl group of said alkylphenol contains from 25 to 100 mole percent predominantly straight-chain alkyl groups of from 15 to 35 carbon atoms and from 75 to 0 mole percent of the alkyl groups are branched-chain, such as polypropenyl, of from 9 to 18 carbon atoms. More preferably, the alkyl group of said alkylphenol contains from 35 to 100 mole percent predominantly straight-chain alkyl groups of from 15 to 35 carbon atoms and from 65 to 0 mole percent of the alkyl groups are branched-chain, such as polypropenyl, of from 9 to 18 carbon atoms. In yet another preferred embodiment, the alkyl group of said alkylphenol contains from 40 to 70 mole percent predominantly straight-chain alkyl groups of from 15 to 35 carbon atoms and from 60 to 30 mole percent of the alkyl groups are branched-chain, such as polypropenyl, of from 9 to 18 carbon atoms. Most preferably, the alkyl group of said alkylphenol contains approximately 50 mole percent predominantly straight-chain alkyl groups of from 15 to 35 carbon atoms and approximately 50 mole percent of the alkyl groups are branched-chain, such as polypropenyl, of from 9 to 18 carbon atoms.

The preferred oil-soluble Group II metal overbased natural or synthetic hydrocarbyl sulfonic acid, sulfonate, or mixture thereof useful for the process of the present invention are single-ring alkyl aromatic hydrocarbyl sulfonic acid, sulfonate, or mixture thereof, more preferred are alkylbenzene or alkyltoluene sulfonic acids, sulfonates or mixtures thereof. The alkyl group on the aromatic ring can be from about 6 to about 60 carbon atoms. Preferably, the alkyl group is from about 10 to about 40 carbon atoms and most preferably from about 20 to about 28 carbon atoms.

The alkyl group of the mono-alkyl or di-alkyl substituted ethylene carbonate useful for carrying out the process of the present invention is preferably a mono-substituted methyl group, i.e., the alkylene carbonate is propylene carbonate. Most preferably, the alkylene carbonate is ethylene carbonate.

The process of the instant invention is particularly useful for preparing highly overbased sulfurized alkylphenols possessing a Total Base Number of greater than about 240, and preferably from about 250 to about 350, more preferably from about 260 to about 290.

In the process of the present invention, the Group II metal oxide, hydroxide or $C_1$-$C_6$ alkoxide is selected from the group consisting of calcium, barium, magnesium and strontium oxide, hydroxide or $C_1$-$C_6$ alkoxide and mixtures thereof. Preferably, the Group II metal oxide, hydroxide or $C_1$-$C_6$ alkoxide is Dolomite comprising $Ca(OH)_2 \cdot Mg(OH)_2$. Most preferably, the Group II metal oxide, hydroxide or $C_1$-$C_6$ alkoxide is calcium hydroxide.

As used herein, the term "Group II metal" means calcium, barium, magnesium, and strontium. Preferably, the Group II metal is selected from the group consisting of calcium, magnesium, barium, and mixtures thereof. Most preferably, the Group II metal is calcium.

In the present process, the alkanol contains at least 6 carbon atoms, and typically from about 8 to about 13 carbon atoms. Preferably, the alkanol is isodecyl alcohol.

The charge mole ratio of the sulfur to the alkylphenol added in step (b) is about 1.0 to about 1.7, preferably about 1.2 to about 1.6, and more preferably about 1.3 to about 1.5.

The $C_2$-$C_{10}$ alkylene glycol of the present process is preferably ethylene glycol.

The process of the present invention may be carried out in a batch or a continuous process. It is believed that small changes in pressure will have little effect on the carbonation process of the present invention.

The present invention is also directed to the novel and unexpected discovery that the Group II metal overbased sulfurized alkylphenol products made when the carbonation step is carried out using ethylene carbonate have superior properties of low color, 3.5 or lower, as measured using ASTM Test No. D 6045, and hydrolytic stability as measured by a modification of ASTM Test No. 2619, as defined below, wherein the TBN of the Group II metal overbased sulfurized alkylphenols decreases less than 10 percent, and preferably less than 8 percent, after the addition of 2.0 percent water and after 6 days at 80° C.

Hydrolytic instability occurs when water is present, but exclusion of water from most systems is impossible. It is also known that overbased sulfurized alkylphenol compositions with high TBN, greater than 250, results in increased hydrolytic instability and increased viscosity. Hydrolytic stability of the Group II metal overbased sulfurized alkylphenols is an extremely important property, particularly in marine crankcase use where water exposure is common. Accordingly, there is a need to develop high TBN Group II metal overbased sulfurized alkylphenol compositions that are hydrolytically stable.

Low color is known to be a very desirable characteristic in commercial lubricating oil additives, including detergents and dispersants. It has been discovered that the Group II metal overbased sulfurized alkylphenol compositions of the present invention have low color in comparison with the prior art preparations. Furthermore, we have found that the amount of sulfur added during the sulfurization step for the preparation of the sulfurized alkylphenol in the present process has no discernable effect on its color.

The present invention is also directed to a process for the in situ delivery of equimolar quantities of alkylene glycol and carbon dioxide to a reaction mixture, wherein said reaction mixture requires the presence of said alkylene glycol and said carbon dioxide as reactants, said process comprising delivering to said reaction mixture:

an alkylene carbonate selected from ethylene carbonate or a mono-alkyl or di-alkyl substituted ethylene carbonate having the following structure:

wherein $R_1$ and $R_2$ are independently hydrogen or alkyl containing one to three carbon atoms; in the presence of water; and under reaction conditions sufficient to hydrolyze the alkylene carbonate to alkylene glycol and carbon dioxide.

Preferably, the hydrolysis of the alkylene carbonate to the alkylene glycol and carbon dioxide is carried out at a temperature in the range of about 150° C. to about 215° C.

DETAILED DESCRIPTION OF THE INVENTION

Definitions

As used herein, the following terms have the following meanings unless expressly stated to the contrary:

The term "alkoxide" means a compound which can be formed as the reaction product of an alcohol and a reactive metal.

The term "alkylene glycol" means an aliphatic diol having two hydroxy groups on adjacent carbon atoms.

The term "alkylphenol" means a phenol group having one or more alkyl substituents, at least one of which has a sufficient number of carbon atoms to impart oil solubility to the phenol.

The term "hydrocarbyl sulfonate" means a sulfonate having one or more sulfonate groups having one or more hydrocarbyl substituents.

The term "hydrolytic stability" means the stability of Group II overbased sulfurized alkylphenols in the presence of water at elevated temperatures. ASTM Test No. 2619 was modified for determining the hydrolytic stability of the Group II overbased sulfurized alkylphenols. The following protocol was followed for all hydrolytic stability determinations:

Group II overbased sulfurized alkylphenols samples were placed in commercial finished marine oil to obtain a final TBN of 8 for the samples. Water ranging from 0% to 2.0% was added to the samples drop-wise at a rate of 0.5 gram per minute while agitating the samples with a peristaltic pump at a rate of 500 rpm. Agitation of the samples at 500 rpm was continued for an additional 10 minutes after the addition of the water. The samples were covered to prevent loss of water and placed in an oven at 80° C. for 6 days. An aliquot of the top layer of the samples containing the oil was carefully removed to determine the TBN using ASTM Test No. D 2896.

Use of the term "ethylene carbonate" includes alkyl-substituted alkylene carbonate, such as propylene carbonate and the like.

The term "overbased" means alkaline earth metal alkylphenols in which the ratio of the number of equivalents of an alkaline earth metal to the number of equivalents of the alkylphenol is greater than 1.

The term "reacting equivalent" means any material equivalent to ethylene glycol and carbon dioxide, such as the carbonic acid half ester.

The term "sulfurization agent" means a material capable of sulfurizing the alkylphenols of the present invention.

The term "Total Base Number" or "TBN" refers to the amount of base equivalent to milligrams of KOH in one gram of sample. Thus, higher TBN numbers reflect more alkaline products, and therefore a greater alkalinity reserve. The TBN of a sample can be determined by ASTM Test No. D 2896 or any other similar procedure.

Unless otherwise specified, all percentages are in weight percent and the pressure is atmospheric pressure.

As noted above, this invention is directed to a novel process for the rapid carbonation of sulfurized alkylphenates using ethylene carbonate or alkylene-substituted ethylene carbonate. We have discovered ethylene carbonate in the carbonation step for the preparation of overbased sulfurized alkylphenates can be used as both a source of carbon dioxide and ethylene glycol. Under the reaction conditions using ethylene carbonate, carbonation time is reduced from 6 hours to less than 1 hour, thus reducing the total preparation time for making overbased sulfurized alkylphenols to nearly one-half the time necessary in the prior art processes.

The present process overcomes many of the limitations of time and temperature control that are critical in the conventional carbonation process. This new process produces carbon dioxide in a highly reactive form that is also better dispersed.

The presence of glycol is essential for good overbasing. Glycol is not merely a solvent but rather plays an active role in phenate carbonation. The in situ production of glycol in the present process provides timely and sufficient glycol for the carbonation process and overcomes the problems encountered in the prior art processes.

In the prior art carbonation process, reaction conditions, especially temperature, must be carefully monitored to avoid "starving" the reaction of glycol. In the present process, no similar issue of glycol starvation is observed. Without being bound by any theory, it is believed that this may be true because carbon dioxide and ethylene glycol are chemically bound in the form of a carbonic acid half ester of ethylene glycol, as will be described later.

Such an intermediate, if present, means that there is always adequate glycol during carbonation. It has now been discovered that ethylene carbonate may be added over 15 minutes at about 186° C. with virtually no loss of carbon dioxide and no adverse effect on crude product sediment, TBN or other critical analytical results.

It has now been found that ethylene carbonate can be added extremely rapidly during carbonation with negligible escape of gaseous carbon dioxide from the reaction. Although there is some remaining hydrogen sulfide gas evolution during the carbonation step, there is very little carbon dioxide evolution. In one experiment, we added ethylene carbonate over a 15-minute period starting at about 177° C. Even with such rapid addition, essentially no carbon dioxide evolution occurred as demonstrated by the low crude product sediment (0.8%). It is believed that if the carbon dioxide escapes, then less $Ca(OH)_2$ is incorporated in the product, thus, resulting in higher sediment. Lack of significant carbon dioxide evolution was also observed as measured by a dry test meter for measuring gas. The explanation for the high carbon dioxide incorporation may involve a mechanism wherein carbon dioxide is not present as such but rather an intermediate half ester of carbonic acid, explained in greater detail below, acts as the carbonation source.

The prior art carbonation process produces one molar equivalent of water for an equimolar reaction of $Ca(OH)_2$ with carbon dioxide. In the prior art processes for making overbased sulfurized alkylphenols, the carbonate is incorporated in a complex form and not simply as calcium carbonate. However, for simplicity, we can represent the formation of calcium carbonate from $Ca(OH)_2$ and carbon dioxide as:

$Ca(OH)_2 + CO_2 \rightarrow$ Calcium Carbonate + Water

By contrast, the present process requires one water molecule to react with the ethylene carbonate to form carbon dioxide and ethylene glycol (or the carbonic acid half ester). The net effect is that the present process both produces and consumes an equal quantity of water, thus eliminating the need to remove water.

The water produced during carbonation is generated at a temperature well above the boiling point of water. For this reason, the carbonation temperature must be carefully selected to facilitate water removal, thus driving the reaction to completion. However, if the temperature is too high, excessive quantities of glycol will steam distill putting the reaction on a path toward glycol starvation.

In the prior art carbonation process employing ethylene glycol and carbon dioxide, carbon dioxide reacts with $Ca(OH)_2$ to form carbonate and water. Without being bound by any theory, it is believed that when ethylene carbonate is the source for carbon dioxide and ethylene glycol, no net water is produced during the formation of the sulfurized alkylphenate carbonate. This may be explained by equations (1) and (2) below. Thus, the consumption of $Ca(OH)_2$ to form carbonate is accompanied by the formation of one molar equivalent of water. Likewise, the hydrolysis of ethylene carbonate to form glycol and carbon dioxide consumes one molar equivalent of water. As shown in equation (3), the overall reaction equation of $Ca(OH)_2$ reacting with ethylene carbonate forms calcium carbonate without formation of water.

(1)

(2)

(3)

Accordingly, the above reactions may explain why water is not formed during the present carbonation process. However, the above equations are a simplification since in the actual process the carbonate is part of an alkylphenate structure rather than a simple salt of calcium. It has now been found that the carbonation of the present process proceeds well even at temperatures up to about 200° C. with little or no loss of carbon dioxide. Furthermore, carbonation with ethylene carbonate proceeds at a remarkably fast rate for temperatures in the range of about 162° C. to about 200° C. This was not anticipated. The general thinking prior to this invention was that consumption of particulate lime, as well as incorporation of oxidized glycol intermediates, within the alkylphenate structure would rate limit the carbonation process. The very rapid carbonation reaction with ethylene carbonate is notably different and produces nearly the same level of carbon dioxide incorporation under varying conditions of temperature and ethylene carbonate addition rate.

Without being bound by any theory, it is predicted that the reaction of ethylene carbonate with water may proceed by either of two paths as shown below. The first step is the hydrolytic cleavage of the cyclic carbonate ring (accelerated by base catalysis) to form a half ester of carbonic acid (4). Intermediate (4) may subsequently react with lime to form the calcium salt (5) or may fragment further to form carbon dioxide and ethylene glycol. For temperatures below about 200° C., formation of intermediate (5) is probably favored over free carbon dioxide and ethylene glycol. When the ethylene carbonate addition temperature is increased in excess of about 200° C., there is a reduction in the phenate carbonate level, which we attribute to the formation of free carbon dioxide and its subsequent partial lost through the reaction vent.

This mechanistic interpretation is logical in terms of an expected rapid neutralization of intermediate (4) with $Ca(OH)_2$ and is further supported by the observation of rapid and complete phenate carbonation which is essentially insensitive to the reaction conditions of time and temperature.

(4)

-continued carbonic acid half ester (5)

Thus, calcium salt (5) is the chemical species that may be responsible for delivering incipient carbon dioxide and ethylene glycol to the sulfurized phenate intermediate. Intermediate (5) may also explain why ethylene glycol is not readily lost from the reaction mixture even at about 200° C. Traditional sulfurized phenate carbonation is limited by conditions of reaction temperature owing to steam distillation of ethylene glycol from the reaction medium. Under conditions of ethylene glycol "starvation", sulfurized phenate reactions are known to give low carbon dioxide incorporation and an increase in the crude product sediment.

The percentage of carbon dioxide incorporation relative to a value calculated assuming quantitative hydrolysis of ethylene carbonate to carbon dioxide and ethylene glycol may be determined for the process of the present invention.

This value remains fairly constant in a range of 92% to 96%. This high efficiency for carbonate formation is likely a result of the efficiency of ethylene carbonate hydrolysis rather than the efficiency in carbon dioxide trapping, which also explains why very rapid ethylene carbonate addition rates do not significantly alter the percentage of carbon dioxide formation.

A simplified molecular structure for an overbased sulfurized carbonate alkylphenate is shown below. For this structure, there would be three basic sites per mole of alkylphenol as shown. From reaction stoichiometry and product analytical data for various overbased sulfurized alkylphenate samples, it has been found that, on average, they contain 3.4 basic sites per mole of alkylphenol. Additional basic sites, not shown in the simplified overbased sulfurized carbonate alkylphenate, include the glycol residues (oxylates, glycolates, etc.) that form an integral part of the phenate structure.

Ethylene Carbonate Carbonation

The rate of addition of ethylene carbonate has been tested over a range of addition times (15 to 120 minutes) and temperature (162° C.-200° C.). The incorporation of carbonate and crude product sediment are relatively immune to these differences in reaction conditions. The addition of ethylene carbonate is relatively exothermic and this can be seen when the ethylene carbonate is added very rapidly (for example, in less than 20 minutes). Under such conditions, that reaction temperature will rise rapidly from about 162° C. (the start of ethylene carbonate addition). At approximately 186° C., some excess foaming was observed. However, even under these conditions, the incorporation of carbonate is very high. On the other hand, ethylene carbonate addition at temperatures in excess of 210° C. should be avoided since an increase in reaction gas evolution and some reduction in the level of product carbonate was observed at these high temperatures. At temperatures above about 200° C., the breakdown of the carbonic acid half ester (1) to carbon dioxide and ethylene glycol appears to be reaction rate competitive with neutralization of the acid to the calcium salt (2).

The reduction in the time for the preparation of overbased sulfurized alkylphenates results in doubling the capacity for production of the overbased sulfurized alkylphenates, without any loss in the quality of the product by infrared spectral analysis. The chemical and physical properties of the product of the present process are also good, including high base content, low crude product sediment and fast filtration rates.

Most surprising was the discovery that the product of the present invention has increased hydrolytic stability and low color. Both hydrolytic stability and low color are extremely desirable and important characteristics for commercial Group II overbased sulfurized alkyl phenol compositions. The product of the present invention has increased hydrolytic stability, as measured by a modification of ASTM Test No. D 2619, as defined above, compared to the prior art product even after 6 days at 80° C. after the addition of water. Lower color, as measured by ASTM Test No. D 6045, is also observed in the Group II overbased sulfurized alkyl phenol compositions of the present invention as compared to those prepared by the prior art processes.

EXAMPLES

Test Example 1

Preparation of an Overbased Sulfurized Alkylphenols

Into a 4 liter, 5-neck resin kettle equipped with a turbine blade stirrer, the following components were combined:
858.5 grams of $C_{10}$-$C_{15}$ alkylphenol
94.4 grams of alkylbenzene sulfonate, wherein the alkyl group on the benzene is 80 percent straight-chain $C_{20}$-$C_{24}$ and 20 percent branched-chain $C_{10}$-$C_{15}$
5.0 grams of defoamer, polydimethysiloxane, Dow Corning 200® purchased from Dow Corning
486.9 grams of isodecyl alcohol.

The contents of the kettle were stirred to 600 rpm and the temperature was ramped to 149° C. over a period of 1 hour. When the temperature reached 40° C. to 50° C., the following additional components were added to the kettle:
402.5 grams of calcium hydroxide
134.1 grams of sulfur
537.4 grams of 150 Neutral oil.

When the temperature of the reaction mixture reached between 68° C. to 70° C., a vacuum of about 740 mm Hg was applied to the kettle with the stirring increased to 800 rpm.

The reaction mixture was held at 149° C. for 30 minutes. Next, 247.9 grams of ethylene glycol was added to the reaction mixture over a period of one hour.

After the addition of ethylene glycol, the temperature was increased from 149° C. to 177° C. over the next hour.

270.9 grams of ethylene carbonate was added to the reaction mixture over 2 hours. After the addition of ethylene carbonate, the temperature was increased from 177° C. to 210° C. over the next 30 minutes and the vacuum was increased from 730 mm Hg to 30 mm Hg over the next 15 to 20 minutes.

The reaction mixture was then held at 210° C. and 30 mm Hg for 30 minutes after which the vacuum was broken with nitrogen gas.

The product was collected after filtration. The product had a TBN of 259 and crude product sediment of 1.6%.

The results of Test Examples 2-6 and Comparative Examples B and C depicted in Table II illustrate the effects of varying certain parameters and reaction conditions when ethylene carbonate is used in the carbonation step.

Test Example 2

Effect of Reduction of Ethylene Glycol on Preparation of Overbased Sulfurized Alkylphenols The procedure set forth above in Test Example 1 was followed, except the amount of ethylene glycol was reduced by 50 weight percent, that is, 244.5 grams was added to the reaction mixture. The results in Table II show that reduction in ethylene glycol is compensated for by the production of ethylene glycol from the hydrolysis of ethylene carbonate, thus there was no appreciable increase in the crude product sediment, 1.9%. A TBN of 255 was obtained for the product.

Test Example 3

Effect of a 10% Reduction and an Increase in the Addition Rate of Ethylene Carbonate on Preparation of Overbased Sulfurized Alkylphenates The procedure set forth above in Test Example 1 was followed, except the amount of ethylene carbonate was reduced by 10% with a concomitant increase in the rate of the addition of ethylene carbonate to the reaction mixture. 220 grams of ethylene carbonate was added over a period of 1 hour instead of 2 hours as in Example 1. The results in Table II show that the rapid addition of ethylene carbonate appears to improve carbonation as seen by low crude product sediment, 0.8% and a higher TBN of 265.

Test Example 4

Effect of Reduced Amount of Isodecyl Alcohol on Preparation of Overbased Sulfurized Alkylphenols The procedure set forth above in Test Example 3 was followed, except the amount of isodecyl alcohol was reduced. The ratio of isodecyl alcohol to lime was 0.9 instead of 1 as in Test Example 1. The results in Table II show that the reduction of isodecyl alcohol to 0.9 of the amount of $Ca(OH)_2$ does not increase the crude product sediment as was seen in Comparative Example B when the isodecyl alcohol was added in a ratio of 0.6 to the amount of lime. The crude product sediment was 1.00% and the TBN was 260.

Test Example 5

Effect of Increase in the Addition Rate of Ethylene Carbonate on the Preparation of Overbased Sulfurized Alkylphenols The procedure set forth above in Test Example 3 was followed, except that ethylene carbonate was added in half the time, 30 minutes instead of 60 minutes. The results in Table II show that the crude product sediment and the TBN do not change appreciably from that obtained in Example 3.

Test Example 6

Effect of Elimination of the Hydrocarbyl Sulfonate on the Preparation of Overbased Sulfurized Alkylphenols The procedure set forth above in Test Example 5 was followed, except that no hydrocarbyl sulfonate was added to the reaction mixture. The results in Table II show that the crude product sediment increased to 4.8% and the TBN decreased to 250.

Test Example 7

Effect of a Further Increase in the Addition Rate of Ethylene Carbonate on the Preparation of Overbased Sulfurized Alkylphenols The procedure set forth above in Test Example 3 was followed, except that ethylene carbonate was added in 15 minutes. The results in Table II show that the ethylene carbonate can be added extremely rapidly in the present process. There is little escape of carbon dioxide as long as the addition of ethylene carbonate is below 210° C. The crude product sediment was 0.8% and the TBN was 263. In addition, the filtration of the crude product was relatively fast.

Comparative Example A

Preparation of Overbased Sulfurized Alkylphenols Using Ethylene Glycol and Carbon Dioxide Overbased sulfurized alkylphenols were prepared as in Test Example 1 above, except the addition of ethylene carbonate was replaced with additions of carbon dioxide and ethylene glycol. The mole ratios of the components of the reaction mixture were kept the same as used in Test Example 1. The results in Table II show a crude product sediment of 1.2% and a TBN of 249.

Comparative Example B

Effect of Isodecyl Alcohol on Preparation of Overbased Sulfurized Alkylphenols when Carbonation is Carried Out Using Ethylene Carbonate The procedure set forth above in Test Example 1 was followed, except the amount of isodecyl alcohol was reduced by 50%, that is, 243.4 grams was added to the reaction mixture. The results in Table II show that the isodecyl alcohol plays a role in the preparation of the overbased sulfurized alkylphenates beyond simply reducing the viscosity of the uncarbonated product. Reduction of isodecyl alcohol may cause high crude product sediment levels, 42%, which is probably a result of poor dehydration and sulfurization. The TBN was also lower, 243.

Comparative Example C

Effect of Ethylene Glycol on Preparation of Overbased Sulfurized Alkylphenols when Carbonation is Carried Out Using Ethylene Carbonate The procedure set forth above in Test Example 1 was followed, except that ethylene glycol was eliminated from the dehydration and sulfurization step in the preparation of the overbased sulfurized alkylphenates. The only ethylene glycol available in the reaction mixture was from the hydrolysis of ethylene carbonate added in the carbonation step. The results show that ethylene glycol is required for the dehydration and sulfurization step prior to the carbonation step. The crude product sediment was 24% and the TBN obtained was 66.4.

The experimental conditions used in Test Examples 1-7 and the Comparative Examples A-C are summarized below in Table I.

TABLE I

| | Amount of Reaction Components Charge Mole Ratio relative to the Alkylphenol | | | | | | Addition of EC[1] |
| --- | --- | --- | --- | --- | --- | --- | --- |
| Ex | Alkylphenol | Isodecyl Alcohol | Ethylene Glycol | Calcium Hydroxide | Ethylene Carbonate | Hydrocarbyl Sulfonate | Time in Minutes |
| 1 | 1.000 | 1.000 | 1.300 | 1.766 | 1.000 | 1.000 | 120 |
| 2 | 1.000 | 1.000 | 0.650 | 1.766 | 1.000 | 1.000 | 120 |
| 3 | 1.000 | 1.000 | 0.650 | 1.766 | 0.900 | 1.000 | 60 |
| 4 | 1.000 | 0.745 | 0.650 | 1.766 | 0.900 | 1.000 | 60 |
| 5 | 1.000 | 0.909 | 0.423 | 1.766 | 0.900 | 1.000 | 60 |
| 6 | 1.000 | 0.909 | 0.423 | 1.766 | 0.900 | 1.000 | 30 |
| 7 | 1.000 | 1.000 | 0.650 | 1.766 | 0.900 | 1.000 | 15 |
| A | 1.000 | 1.034 | 1.310 | 1.766 | $CO_2$* 0.893 | 1.000 | NA[2] |
| B | 1.000 | 0.500 | 1.300 | 1.766 | 1.000 | 1.000 | 120 |
| C | 1.000 | 0.909 | 0.0 | 1.766 | 1.000 | 1.000 | 60 |

[1]Ethylene carbonate.
*Carbon dioxide replaced the carbon dioxide obtained from the hydrolysis of ethylene carbonate in the Test Examples.
[2]No ethylene carbonate added.

The results obtained in the above Test Examples 1-7 and the Comparative Examples A-C are given below in Table II.

TABLE II

| | Final Product | Weight Percent of Final Product | | | | |
| --- | --- | --- | --- | --- | --- | --- |
| Ex | Weight in grams | Sulfur | Calcium | $CO_2$ | Sediment | TBN |
| 1 | 2253 | 4.1 | 9.5 | 5.5 | 1.6 | 259 |
| 2 | 2083 | 3.5 | 9.5 | 5.6 | 1.9 | 255 |
| 3 | 2023 | 3.5 | 9.9 | 5.3 | 0.8 | 265 |
| 4 | 2040 | 3.7 | 9.6 | 5.1 | 1.0 | 260 |
| 5 | 1996 | 3.5 | 9.7 | 5.3 | 1.0 | 263 |
| 6 | 2041 | 3.5 | 9.1 | 5.0 | 4.8 | 250 |
| 7 | 2024 | 3.5 | 9.7 | 5.3 | 0.8 | 263 |
| A | 1769 | 3.5 | 9.2 | 5.2 | 1.2 | 249 |
| B | 2291 | 3.6 | 9.0 | 4.9 | 42 | 243 |
| C | 1904 | 2.8 | 2.4 | 0.3 | 24 | 66 |

Hydrolytic Stability Studies

The Group II metal overbased sulfurized alkylphenol products of this invention has increased hydrolytic stability compared to the Group II metal overbased sulfurized alkylphenols prepared using the conventional carbonation process employing ethylene glycol and carbon dioxide.

The hydrolytic stability of the Group II overbased sulfurized alkyl phenol compositions of the present invention was determined using a modification of ASTM Test No. D 2619. The modified test, as defined above, measures the hydrolytic stability of a product by measuring its TBN loss upon exposure to moisture. Greater TBN loss reflects poorer hydrolytic stability.

Figure 1:
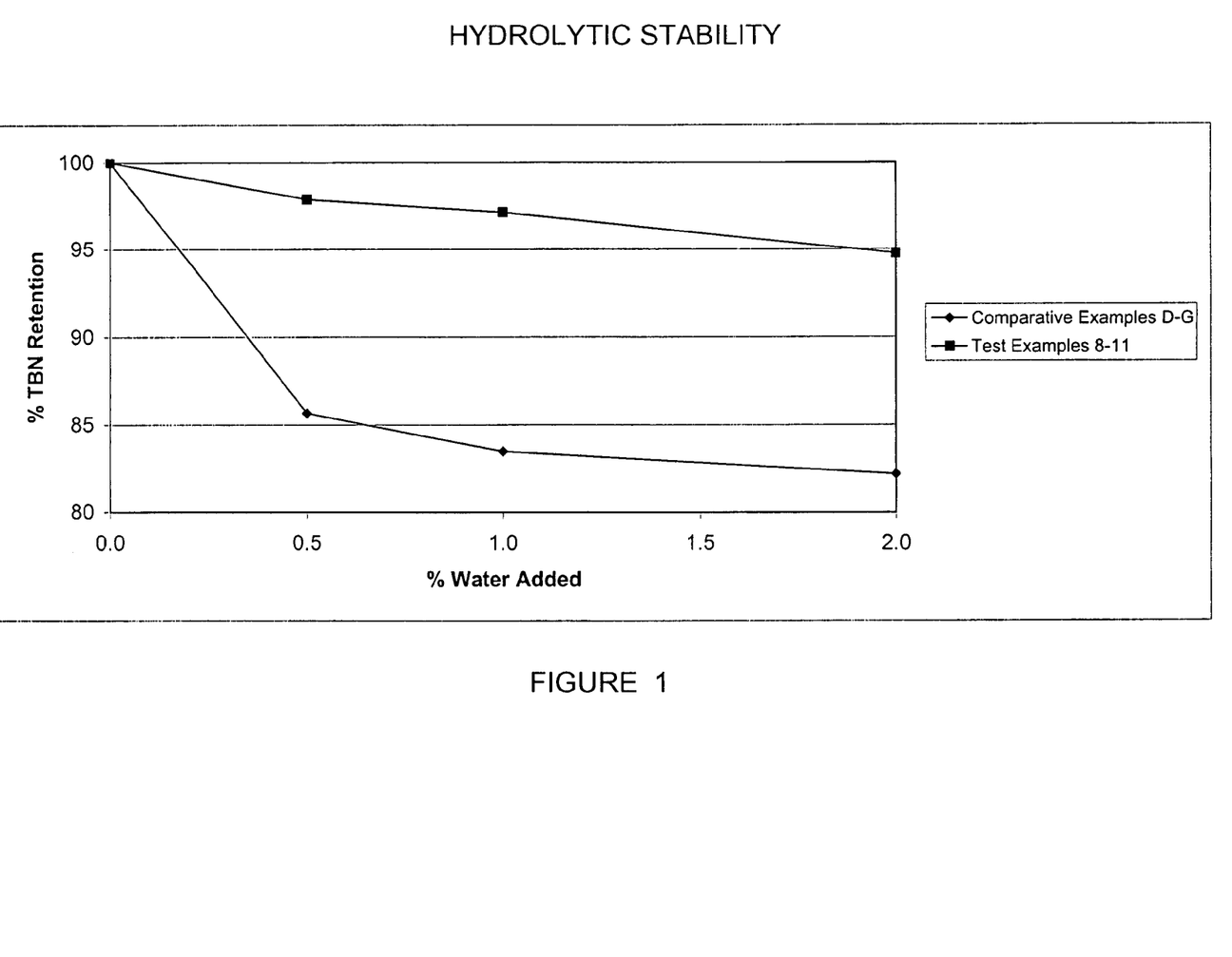
FIG. 1 shows a comparison of the effect of the addition of water on the hydrolytic stability, represented by the percent TBN retained, of Test Examples 1-4, the products of the present invention, and Comparative Examples D-G. The data used to prepare FIG. 1 are also shown in Table III in the Examples section.

Hydrolytic stability data were collected in experiments where water was added to the overbased sulfurized alkylphenol samples and the retention of TBN was measured. The data given in Table III below and in FIG. 1 show that the overbased sulfurized alkylphenols prepared by the process of the present invention are more hydrolytically stable than those prepared using the conventional carbonation process as demonstrated by the percent of TBN retention.

Comparative Examples D-G were prepared using the procedure of Comparative Example A above. Test Examples 8-11 were prepared using the procedure of Test Example 1 above. Tests were conducted with and without the addition of water. The results of the tests are given in Table III and in FIG. 1.

TABLE III

HYDROLYTIC STABILITY

| Examples | Amount of Water Added to Blend | TBN of Sample after 6 Days at 80° C. | Percent TBN Retention |
| --- | --- | --- | --- |
| D | 0.0 wt. % | 7.4846 | 100 |
| E | 0.5 wt. % | 6.4115 | 85.66 |
| F | 1.0 wt. % | 6.2482 | 83.48 |
| G | 2.0 wt. % | 6.1505 | 82.18 |
| 8 | 0.0 wt. % | 6.8373 | 100 |
| 9 | 0.5 wt. % | 6.6935 | 97.9 |
| 10 | 1.0 wt. % | 6.6432 | 97.16 |
| 11 | 2.0 wt. % | 6.4792 | 94.76 |

The results of the hydrolytic stability studies clearly show that the Group II overbased sulfurized alkylphenols prepared by the process of the present invention have consistently better TBN retention than that observed for the Group II overbased sulfurized alkylphenols of Comparative Examples D-G.

Color Studies

Color studies were conducted to determine the degree of color of the Group II overbased sulfurized alkylphenols prepared by the process of the present invention as compared to that of the Group II overbased sulfurized alkylphenols prepared using ethylene glycol and carbon dioxide.

Test Examples 12-19 were prepared using the procedure of Test Example 1. Comparative Examples H-L were commercial Group II sulfurized alkylphenols prepared from $C_{10}$-$C_{15}$ alkylphenol using ethylene glycol and carbon dioxide.

Figure 2:
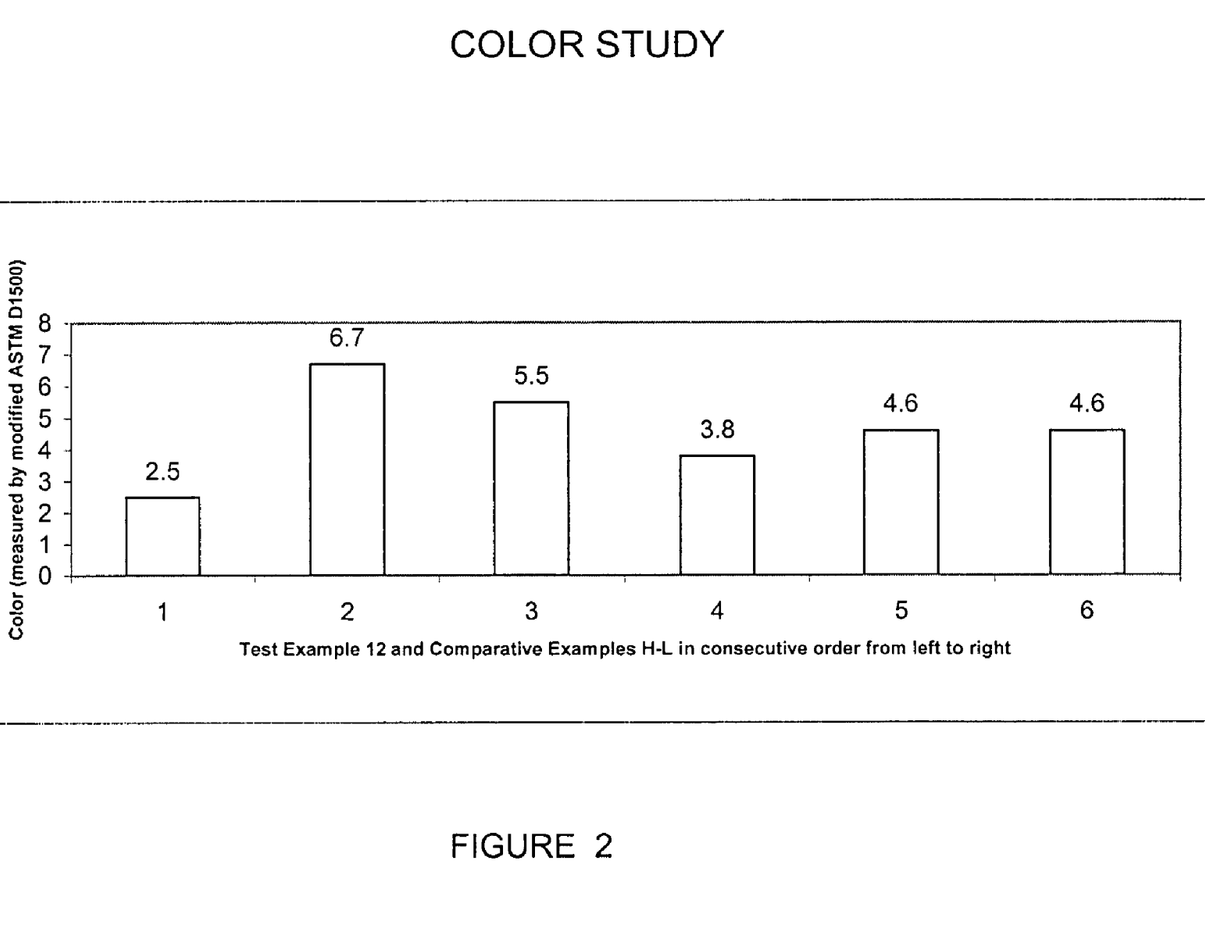
FIG. 2 shows a comparison of color measurements for Test Example 12 and Comparative Examples H-L.

Color was determined using ASTM Test No. D 6045. The results obtained using a Lovibond PFX995 Tintometer are given in Table IV and FIG. 2.

The results show that the Group II metal overbased sulfurized alkylphenol products prepared by the process of this invention, Test Example 12, have less color than observed for the commercial Group II metal overbased sulfurized alkylphenols, Comparative Examples H-L.

The effect of sulfur concentration on the amount of color was also determined using ASTM Test No. D 6045. The experimental results given in Table IV below show that under the standard experimental conditions (see Test Example 1 above), reduction in sulfur during the sulfurization step of the present process does not reduce the color of the overbased sulfurized alkylphenol products prepared by the process of the present invention, Test Examples 13-19.

TABLE IV

| | Sulfur | | COLOR | | | |
|---|---|---|---|---|---|---|
| Example | CMR* | TBN | Sample 1 | Sample 2 | Sample 3 | Average |
| 12 | 1.36 | 259 | 2.5 | 2.5 | 2.5 | 2.5 |
| 13 | 1.29 | 259 | 3.4 | 3.5 | 3.5 | 3.5 |
| 14 | 1.25 | 258 | 3.0 | 3.0 | 3.0 | 3.0 |
| 15 | 1.21 | 265 | 3.3 | 3.3 | 3.3 | 3.3 |
| 16 | 1.18 | 262 | 3.0 | 3.0 | 3.0 | 3.0 |
| 17 | 1.10 | 269 | 3.4 | 3.5 | 3.5 | 3.5 |
| 18 | 0.99 | 267 | 3.0 | 3.2 | 3.2 | 3.2 |
| 19** | 0.90 | 252 | — | — | — | Hazy, not bright |
| H | 100 | 250 | 6.5 | 6.9 | 6.8 | 6.7 |
| I | 100 | 250 | 5.5 | 5.5 | 5.6 | 5.5 |
| J | 100 | 250 | 3.8 | 3.8 | 3.8 | 3.8 |
| K | 100 | 250 | 4.6 | 4.6 | 4.7 | 4.6 |
| L | 100 | 250 | 4.6 | 4.6 | 4.6 | 4.6 |

*CMR is charge mole ratio of sulfur to the alkylphenol.
**Color of Test Example 19 could not be determined.

The invention claimed is:

1. A process for preparing Group II metal overbased sulfurized alkylphenols which comprises:

forming a reaction mixture by combining a sulfurized alkylphenol wherein the alkyl group contains a sufficient number of carbon atoms to render oil-soluble the resulting Group II metal overbased sulfurized alkylphenol, an alkanol containing about 6 to about 15 carbon atoms, a Group II metal oxide, hydroxide or $C_1$-$C_6$ alkoxide, a $C_2$-$C_{10}$ alkylene glycol and contacting with an alkylene carbonate selected from ethylene carbonate or a monoalkyl or di-alkyl substituted ethylene carbonate, said alkylene carbonate having the following structure:

wherein $R_1$ and $R_2$ are independently hydrogen or alkyl containing one to three carbon atoms; and wherein the contacting is carried out for a time and at a temperature sufficient to form in situ carbon dioxide and alkylene glycol, or a reacting equivalent, to form a product comprising a Group II earth metal overbased sulfurized alkylphenol.

2. The process of claim 1 wherein the sulfurized alkylphenol is a Group II metal sulfurized alkylphenate.

3. The process of claim 1 further comprising an oil-soluble Group II metal overbased natural or synthetic hydrocarbyl sulfonic acid, sulfonate, or mixtures thereof.

4. The process of claim 1 wherein the alkylene carbonate is added to the reaction mixture over a time period of about 5 minutes to about 120 minutes.

5. The process of claim 4 wherein the alkylene carbonate is added to the reaction mixture over a time period of about 15 minutes to about 90 minutes.

6. The process of claim 5 wherein the alkylene carbonate is added to the reaction mixture over a time period of about 30 minutes to about 60 minutes.

7. The process of claim 1 wherein the temperature is maintained below about 215° C.

8. The process of claim 7 wherein the temperature is maintained between 150° C. and 210° C.

9. The process of claim 1 wherein the alkyl group of the alkylene carbonate is a methyl group.

10. The process of claim 1 wherein the alkylene carbonate is ethylene carbonate.

11. A process for preparing Group II metal overbased sulfurized alkylphenols which comprises the steps of (a) forming a reaction mixture by combining a sulfurized alkylphenol wherein the alkyl group contains a sufficient number of carbon atoms to render oil-soluble the resulting Group II metal overbased sulfurized alkylphenol, an alkanol containing about 6 to about 15 carbon atoms, a Group II metal oxide, hydroxide or $C_1$-$C_6$ alkoxide, and a $C_2$-$C_{10}$ alkylene glycol; and (b) contacting said reaction mixture with an alkylene carbonate selected from ethylene carbonate or a monoalkyl or di-alkyl substituted ethylene carbonate, said alkylene carbonate having the following structure:

wherein $R_1$ and $R_2$ are independently hydrogen or alkyl containing one to three carbon atoms; and wherein the contacting is carried out for a time and at a temperature sufficient to form in situ carbon dioxide and alkylene glycol, or a reacting equivalent, to form a product comprising a Group II earth metal overbased sulfurized alkylphenol.

12. The process of claim 11 wherein the sulfurized alkylphenol is a Group II metal sulfurized alkylphenate.

13. The process of claim 11 further comprising in step (a) an oil-soluble Group II metal overbased natural or synthetic hydrocarbyl sulfonic acid, sulfonate, or mixtures thereof.

14. The process of claim 11 wherein in step (b) the alkylene carbonate is added to the reaction mixture over a time period of about 5 minutes to about 120 minutes.

15. The process of claim 14 wherein in step (b) the alkylene carbonate is added to the reaction mixture over a time period of about 15 minutes to about 90 minutes.

16. The process of claim 15 wherein in step (b) the alkylene carbonate is added to the reaction mixture over a time period of about 30 minutes to about 60 minutes.

17. The process of claim 11 wherein in step (b) the temperature is maintained below about 215° C.

18. The process of claim 17 wherein in step (b) the temperature is maintained between 150° C. and 210° C.

19. The process of claim 11 wherein in step (b) the alkyl group of the alkylene carbonate is a methyl group.

20. The process of claim 11 wherein in step (b) the alkylene carbonate is ethylene carbonate.

21. A process for preparing Group II metal overbased sulfurized alkylphenols which comprises the steps of:
(a) forming a first reaction mixture by combining an alkylphenol wherein the alkyl group contains a sufficient number of carbon atoms to render oil-soluble the resulting Group II metal overbased sulfurized alkylphenol, an oil-soluble Group II metal overbased natural or synthetic hydrocarbyl sulfonic acid, sulfonate, or mixtures thereof, and an alkanol containing about 6 to about 15 carbon atoms, the temperature of said first reaction mixture being at least about 40° C.;
(b) contacting said first reaction mixture with a second reaction mixture comprising a Group II metal oxide, hydroxide or $C_1$-$C_6$ alkoxide; a sulfurization agent and an inert hydrocarbon diluent at a temperature and for a time sufficient to effect sulfurization of the alkylphenol to form a third reaction mixture;
(c) contacting said third reaction mixture with $C_2$-$C_{10}$ alkylene glycol to form a fourth reaction mixture; and
(d) contacting said fourth reaction mixture with an alkylene carbonate selected from ethylene carbonate or a mono-alkyl or di-alkyl substituted ethylene carbonate, said alkylene carbonate having the following structure:

wherein $R_1$ and $R_2$ are independently hydrogen or alkyl containing one to three carbon atoms, and wherein said contacting is carried out for a time and at a temperature sufficient to form in situ carbon dioxide and alkylene glycol, or a reacting equivalent, to form a product comprising a Group II earth metal overbased sulfurized alkylphenol.

22. The process of claim 21 wherein in step (d) the alkylene carbonate is added to the fourth reaction mixture over a time period of about 5 minutes to about 120 minutes.

23. The process of claim 22 wherein in step (d) the alkylene carbonate is added to the fourth reaction mixture over a time period of about 15 minutes to about 90 minutes.

24. The process of claim 23 wherein in step (d) the alkylene carbonate is added to the fourth reaction mixture over a time period of about 30 minutes to about 60 minutes.

25. The process of claim 21 wherein in step (d) the temperature is maintained below about 215° C.

26. The process of claim 25 wherein in step (d) the temperature is maintained between 150° C. and 210° C.

27. The process of claim 21 wherein in step (d) the alkyl group of the alkylene carbonate is a methyl group.

28. The process of claim 21 wherein in step (d) the alkylene carbonate is ethylene carbonate.

29. The process of claim 21 wherein the ratio of the alkylene carbonate to the alkylphenol is 0.6 to 1.5 weight percent.

30. The process of claim 21 wherein the charge mole ratio of the sulfur to the alkylphenol added in step (b) is about 1.0 to about 1.7.

31. The process of claim 30 wherein the charge mole ratio of the sulfur to the alkylphenol added in step (b) is about 1.3 to about 1.5.

32. The process of claim 21 wherein in step (c), after contacting the third reaction mixture with a $C_2$-$C_{10}$ alkylene glycol, the temperature of the system is raised, if necessary, from that of step (b) to between about 120° C. and about 190° C.

33. The process of claim 21 wherein in step (c) the $C_2$-$C_{10}$ alkylene glycol addition is conducted at from about 100° C. to about 190° C.

34. The process of claim 33 wherein in step (c) the $C_2$-$C_{10}$ alkylene glycol addition is conducted at from 125° C. to 165° C.

35. The process of claim 21 further comprising:
(e) heating the fourth reaction mixture of step (d) under reduced pressure to remove a portion of unreacted $C_2$-$C_{10}$ alkylene glycol and carbon dioxide.

36. The process of claim 35 wherein step (e) is preferably conducted at from about 175° C. to about 210° C.

37. The process of claim 21 further comprising in step (a) or in step (b), or in both steps (a) and (b), the presence of a sulfurization catalyst, wherein the sulfurization catalyst is a hydrogen halide, an ammonium halide, a metal halide or 2-mercaptobenzothiozole.

38. The process of claim 37 wherein the sulfurization catalyst is a metal halide.

39. The process of claim 38 wherein the sulfurization catalyst is calcium chloride.

40. The process of claim 21 wherein the alkyl group of the alkylphenol contains from about 25 to about 100 mole percent straight-chain alkyl groups containing from about 15 to about 35 carbon atoms and from about 75 to about 0 mole percent branched-chain alkyl groups containing from about 9 to about 18 carbon atoms.

41. The process of claim 40 wherein the alkyl group of the alkylphenol contains from about 35 to about 100 mole percent straight-chain alkyl groups containing from about 15 to about 35 carbon atoms and from about 65 to about 0 mole percent branched-chain alkyl groups containing from about 9 to about 18 carbon atoms.

42. The process of claim 41 wherein the alkyl group of the alkylphenol contains from about 40 to about 70 mole percent straight-chain alkyl groups containing from about 15 to about 35 carbon atoms and from about 60 to about 30 mole percent branched-chain alkyl groups containing from about 9 to about 18 carbon atoms.

43. The process of claim 42 wherein the alkyl group of the alkylphenol contains approximately 50 mole percent straight-chain alkyl groups containing from about 15 to about 35 carbon atoms and approximately 50 mole percent branched-chain alkyl groups containing from about 9 to about 18 carbon atoms.

44. The process of claim 21 wherein the alkyl group of the alkylphenol is attached predominantly at the para position of the phenol ring.

45. The process of claim 44 wherein the alkylphenol containing the para attachment of the alkyl group is from about 70 to about 95 weight percent of the total alkylphenol.

46. The process of claim 45 wherein the alkylphenol containing the pare attachment of the alkyl group is from about 80 to about 95 weight percent of the total alkylphenol.

47. The process of claim 21 wherein the alkanol contains about 8 to about 13 carbon atoms and the $C_2$-$C_{10}$ alkylene glycol is ethylene glycol.

48. The process of claim 47 wherein the alkanol is isodecyl alcohol.

49. The process of claim 21 wherein the hydrocarbyl group of the oil-soluble Group II metal overbased natural or synthetic hydrocarbyl sulfonic acid, sulfonate, or mixtures thereof, is an alkyl aromatic group.

50. The process of claim 49 wherein the alkyl group of the alkyl aromatic group contains from about 6 carbon atoms to about 60 carbon atoms.

51. The process of claim 50 wherein the alkyl group of the alkyl aromatic group contains from about 10 carbon atoms to about 40 carbon atoms.

52. The process of claim 51 wherein the alkyl group of the alkyl aromatic group contains from about 20 carbon atoms to about 28 carbon atoms.

53. The process of claim 21 wherein the Group II metal oxide, hydroxide or $C_1$-$C_6$ alkoxide is selected from the group consisting of calcium, barium, and magnesium oxide, hydroxide or $C_1$-$C_6$ alkoxide and mixtures thereof.

54. The process of claim 53 wherein the Group II metal oxide, hydroxide or $C_1$-$C_6$ alkoxide is calcium hydroxide.

55. The process of claim 54 wherein the Group II metal oxide, hydroxide or $C_1$-$C_6$ alkoxide is Dolomite comprising $Ca(OH)_2 \cdot Mg(OH)_2$.

56. A product made by the process of claim 1.

57. A product made by the process of claim 11.

58. A product made by the process of claim 21.

59. A product made by the process of claim 35.

60. A product made by the process of claim 37.

61. A detergent-dispersant additive comprising Group II metal overbased sulfurized alkylphenols, said additive being characterized by the following properties:
   (a) a color of 3.5 or lower, as measured using ASTM Test No. D 6045; and
   (b) an increased hydrolytic stability as measured by a modified ASTM Test No. 2619 wherein the TBN of the Group II metal overbased sulfurized alkylphenols decreases less than 10 percent after dilution of the Group II metal overbased sulfurized alkylphenols in finished marine oil to a TBN of 10 and the addition of 2.0 percent water and after 6 days at 80° C.

62. The detergent-dispersant additive of claim 61 wherein the TBN of the Group II metal overbased sulfurized alkylphenols decreases less than 8 percent after dilution of the Group II metal overbased sulfurized alkylphenols in finished marine oil to a TEN of 8 and the addition of 2.0 percent water and after 6 days at 80° C.

* * * * *